(12) United States Patent
Barclay et al.

(10) Patent No.: US 7,022,454 B2
(45) Date of Patent: Apr. 4, 2006

(54) MONOMERS, POLYMERS, METHODS OF SYNTHESIS THEREOF AND PHOTORESIST COMPOSITIONS

(75) Inventors: George G. Barclay, Jefferson, MA (US); Wang Yueh, Portland, OR (US); Joseph Mattia, Framingham, MA (US)

(73) Assignee: Shipley Company, L.L.C., Marlborough, MA (US)

( * ) Notice: Subject to any disclaimer, the term of this patent is extended or adjusted under 35 U.S.C. 154(b) by 0 days.

(21) Appl. No.: 09/794,301

(22) Filed: Feb. 26, 2001

(65) Prior Publication Data

US 2002/0013448 A1   Jan. 31, 2002

Related U.S. Application Data

(60) Provisional application No. 60/185,339, filed on Feb. 26, 2000.

(51) Int. Cl.
  *G03F 7/004*   (2006.01)
  *G03C 1/492*   (2006.01)
  *G03C 5/00*   (2006.01)

(52) U.S. Cl. .................. 430/270.1; 430/326; 430/908

(58) Field of Classification Search ............. 430/270.1, 430/326, 910
See application file for complete search history.

(56) References Cited

U.S. PATENT DOCUMENTS 6,147,249 A * 11/2000 Watanabe et al. .......... 560/120
6,284,429 B1 * 9/2001 Kinsho et al. .......... 430/270.1

FOREIGN PATENT DOCUMENTS

EP    0 520 419    12/1992
GB    2 332 902    7/1999

* cited by examiner

*Primary Examiner*—Rosemary Ashton
(74) *Attorney, Agent, or Firm*—Peter F. Corless; Darryl P. Frickey; Edwards Angell Palmer & Dodge

(57) ABSTRACT

The present invention provides novel alicyclic-esterified norbornene carboxylates monomers, polymers and photoresist compositions that comprise the polymers as a resin binder component. Methods for synthesis of the monomers and polymers of the invention are also provided. The photoresist compositions of the invention can provide highly resolved relief images upon exposure to short wavelengths, including sub-300 and sub-200 nm wavelengths such as 193 nm and 157 nm.

15 Claims, No Drawings

MONOMERS, POLYMERS, METHODS OF SYNTHESIS THEREOF AND PHOTORESIST COMPOSITIONS

This application claims benefit of Provisional 60/185,339 filed Feb. 26, 2000.

BACKGROUND OF THE INVENTION

1. Field of the Invention

The present invention relates to new monomers and polymers and use of such polymers as a resin binder component for photoresist compositions, particularly chemically-amplified positive-acting resists that can be effectively imaged at short wavelengths such as 248 nm, 193 nm and 157 nm.

2. Background

Photoresists are photosensitive films used for transfer of images to a substrate. A coating layer of a photoresist is formed on a substrate and the photoresist layer is then exposed through a photomask to a source of activating radiation. The photomask has areas that are opaque to activating radiation and other areas that are transparent to activating radiation. Exposure to activating radiation provides a photoinduced chemical transformation of the photoresist coating to thereby transfer the pattern of the photomask to the photoresist-coated substrate. Following exposure, the photoresist is developed to provide a relief image that permits selective processing of a substrate.

A photoresist can be either positive-acting or negative-acting. For most negative-acting photoresists, those coating layer portions that are exposed to activating radiation polymerize or crosslink in a reaction between a photoactive compound and polymerizable reagents of the photoresist composition. Consequently, the exposed coating portions are rendered less soluble in a developer solution than unexposed portions. For a positive-acting photoresist, exposed portions are rendered more soluble in a developer solution while areas not exposed remain comparatively less developer soluble.

In general, photoresist compositions comprise at least a resin binder component and a photoactive agent. Photoresist compositions are described in Deforest, *Photoresist Materials and Processes,* McGraw Hill Book Company, New York, ch. 2, 1975 and by Moreau, *Semiconductor Lithography, Principles, Practices and Materials,* Plenum Press, New York, ch. 2 and 4, both incorporated herein by reference for their teaching of photoresist compositions and methods of making and using the same.

More recently, chemically-amplified-type resists have been increasingly employed, particularly for formation of sub-micron images and other high performance applications. Such photoresists may be negative-acting or positive-acting and generally include many crosslinking events (in the case of a negative-acting resist) or deprotection reactions (in the case of a positive-acting resist) per unit of photogenerated acid. In the case of positive chemically-amplified resists, certain cationic photoinitiators have been used to induce cleavage of certain "blocking" groups pendant from a photoresist binder, or cleavage of certain groups that comprise a photoresist binder backbone. See, for example, U.S. Pat. Nos. 5,075,199; 4,968,581; 4,883,740; 4,810,613; and 4,491,628, and Canadian Patent Application 2,001,384. Upon cleavage of the blocking group through exposure of a coating layer of such a resist, a polar functional group is formed, e.g., carboxyl or imide, which results in different solubility characteristics in exposed and unexposed areas of the resist coating layer. See also R. D. Allen et al., *Proceedings of SPIE,* 2724:334–343 (1996); and P. Trefonas et al. *Proceedings of the 11$^{th}$ International Conference on Photopolymers (Soc. Of Plastics Engineers),* pp 44–58 (Oct. 6, 1997).

While currently available photoresists are suitable for many applications, current resists also can exhibit significant shortcomings, particularly in high performance applications such as formation of highly resolved sub-half micron and sub-quarter micron features.

Consequently, interest has increased in photoresists that can be photoimaged with short wavelength radiation, including exposure radiation of about 250 nm or less, or even about 200 nm or less, such as wavelengths of about 248 nm (provided by KrF laser) or 193 nm (provided by an ArF exposure tool). Use of such short exposure wavelengths can enable formation of smaller features. Accordingly, a photoresist that yields well-resolved images upon 248 nm or 193 nm exposure could enable formation of extremely small (e.g. sub-0.25 µm) features that respond to constant industry demands for smaller dimension circuit patterns, e.g. to provide greater circuit density and enhanced device performance.

However, many current photoresists are generally designed for imaging at relatively higher wavelengths, such as I-line (365 nm) and G-line (436 nm) exposures and are generally unsuitable for imaging at short wavelengths such as 193 nm and 248 nm. In particular, prior resists exhibit poor resolution (if any image at all can be developed) upon exposure to these shorter wavelengths. Among other things, current photoresists can be highly opaque to extremely short exposure wavelengths such as 248 nm and 193 nm, thereby resulting in poorly resolved images. Efforts to enhance transparency for short wavelength exposure can negatively impact other important performance properties such as substrate adhesion, which in turn can dramatically compromise image resolution.

It thus would be desirable to have new photoresist compositions, particularly resist compositions that can be imaged at short wavelengths such as 248 nm, 193 nm and 157 nm.

SUMMARY OF THE INVENTION

The present invention provides novel monomers and polymers and photoresist compositions that comprise the polymers as a resin binder component.

The photoresist compositions of the invention can provide highly resolved relief images upon exposure to extremely short wavelengths, particularly 248 nm and 193 nm. The photoresists of the invention preferably are chemically-amplified positive resists, which utilize photoacid-induced cleavage of pendant alkyl ester polymer groups to provide solubility differentials between exposed and unexposed areas of a resist coating layer.

More particularly, norbornene carboxylate monomers in which the carboxylate functionality is protected by (esterified with) photoacid-labile tertiary alicyclic groups. The alicyclic group can comprise a single ring (e.g. cyclopentyl, cyclohexyl or cycloheptyl), or may be polycyclic, e.g. and contain 2, 3, 4 or more bridged, fused or otherwise linked rings. For instance, preferred monomers of the invention include compounds of the following Formula I:

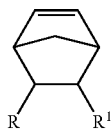

I wherein R and R¹ are independently hydrogen, an ester moiety with a tertiary alicyclic group, optionally substituted alkyl (including cycloalkyl) preferably having from 1 to about 16 carbons, optionally substituted alkoxy preferably having from 1 to about 16 carbons, optionally substituted alkylthio preferably having from 1 to about 16 carbons, and the like, with at least one of R and R¹ being an ester moiety with a tertiary alicyclic group. The one or two ester moieties with tertiary alicyclic group may be directly pendant from the norbornene ring (i.e. —C(=O)OR, where R is a tertiary alicyclic group), or the ester moieties may be spaced from the norbornene ring, e.g. by an optionally alkylene linkage (e.g. . —(CH₂)₁₋₈C(=O)OR, where R is a tertiary alicyclic group). Preferably the one or two ester moieties are directly pendant from the norbornene ring. Preferred tertiary alicyclic ester R and R¹ groups of Formula I are shown below with reference to preferred X groups of Formula II.

Particularly preferred monomers of the invention include compounds of the following Formula II:

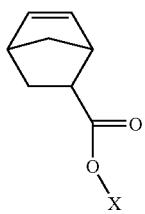

II in which X of that Formula is a tertiary alicyclic group such as the following groups, where the waved line indicates the chemical bond linkage to the norbornene ester oxygen:

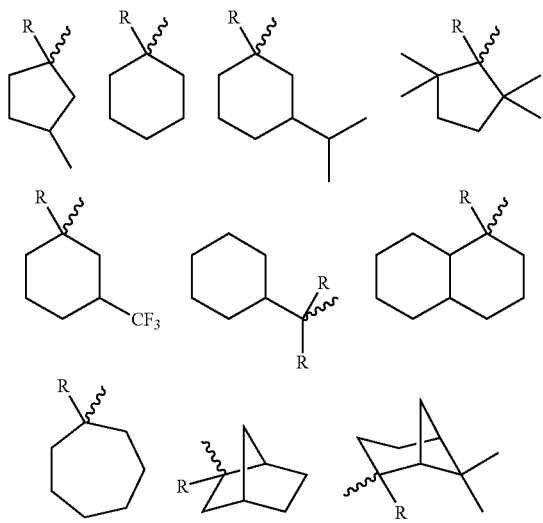

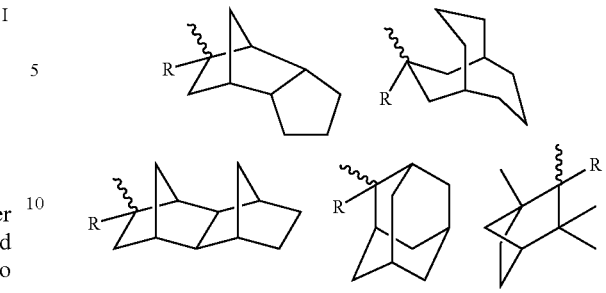

where in the above alicyclic structures R is an optionally substituted alkyl group, particularly $C_{1-16}$ alkyl (including cycloalkyl), more typically $C_{1-6}$ alkyl; optionally substituted alkoxy group, particularly $C_{1-8}$ alkoxy, more typically $C_{1-6}$ alkoxy; or optionally substituted carbocyclic aryl, particularly optionally substituted phenyl.

In general, polymers of the invention comprise one or more polymerized units of the above discussed norbornene carboxylate monomers in which the carboxylate functionality is protected by (esterified with) photoacid-labile tertiary alicyclic groups.

Preferred polymers of the invention contain other repeat units in addition to alicyclic-esterified norbornene carboxylates. For example, preferred polymers may contain units provided by polymerized electron-deficient monomers that may or may not be photoacid-labile, such as an ethylene unsaturated ketone or di-ketone, e.g. an anhydride such as maleic anhydride, itaconic anhydride, citrionic ahydride; amides such as maleimide; esters, particularly lactones; etc.

Additional preferred polymers include those that contain a polymerized acrylate, which may or may not be photoacid-labile. For example, photoacid-labile alkylesters of acrylic acid, methacrylic acid and the like may be polymerized, e.g. t-butyl acrylate or t-butyl methacrylate.

Polymers of the invention may contain other additional units. Additional photoacid-labile groups are preferred in many instances. For example, polymers may contain additional photoacid-labile groups such as pendant esters such as those of the formula —WC(=O)OR⁵, wherein W is a linker such as a chemical bond, an alkylene particularly $C_{1-3}$ alkylene, or carbocyclic aryl such as phenyl, or aryloxy such as phenoxy, and R⁵ is a suitable ester moiety such as an optionally substituted alkyl (including cycloalkyl) suitably having from 1 to about 20 carbons, more preferably about 4 to about 12 carbons, but without a noncyclic or single ring alkyl group having 5 or more carbons and two or more secondary, tertiary or quaternary carbons; optionally substituted alkenyl (including cycloalkenyl) group suitably having from 2 to about 20 carbons, more preferably about 4 to about 12 carbons; optionally substituted alkynyl group suitably having from 2 to about 20 carbons, more preferably about 4 to about 12 carbons; optionally substituted alkoxy group suitably having from 1 to about 20 carbons, more preferably 2 to about 12 carbons; or a heteroalicyclic group that contains one or more N, O or S atoms and one or more rings having from 4 to about 8 ring members such as tetrahydrofuranyl, thienyl, tetrahydropyranyl, morpholino and the like. Specifically preferred R⁵ groups include e.g. t-butyl, tetrahydropyran, ethoxyethyl, or an alicyclic group including bridged groups such as such as adamantyl including 2-methyl-2-adamantyl, norbomyl, isobomyl and the like.

Polymers of the invention optionally may contain other groups that contribute to aqueous developability of a photoresist. For example, preferred polymer groups that contribute to aqueous developability contain carboxy or hydroxy moieties such as may be provided by condensation of vinylaryl such as vinylphenol which may be provided by condensation of vinylphenol, acrylic acid, methacrylic acid, 2-hydroxyethylmethacrylate, or other hydrophilic monomers.

Other optional polymer units include those that may be provided by condensation of a vinyl alicyclic group, e.g. 2-adamantyl-2-methyl methacrylate, isobornyl methacrylate and the like, or a non-cyclic alkyl group such as t-butyl methacrylate and the like as discussed above, or a vinyl nitrile such as condensation of methacrylonitrile to provide pendant cyano groups. Pendant cyano, acid (COOH), and/or alicyclic groups, such as those mentioned above, are often preferred additional units of polymers of the invention.

For use in photoresists to be imaged at sub-200 nm wavelengths such as 193 nm, preferably a polymer of the invention will be substantially free of any phenyl or other aromatic groups. For example, preferred polymers contain less than about 5 or 4 mole percent aromatic groups, more preferably less than about 1 mole percent aromatic groups, more preferably less than about 0.1, 0.02, 0.04 and 0.08 mole percent aromatic groups and still more preferably less than about 0.01 mole percent aromatic groups. Particularly preferred polymers are completely free of aromatic groups. Aromatic groups can be highly absorbing of sub-200 nm radiation and thus are undesirable for polymers used in photoresists imaged with such short wavelength radiation.

The invention also provides methods for forming relief images, including methods for forming a highly resolved relief image such as a pattern of lines where each line has essentially vertical sidewalls and a line width of about 0.40 microns or less, and even a width of about 0.25, 0.20 or 0.16 microns or less. The invention further provides articles of manufacture comprising substrates such as a microelectronic wafer substrate or liquid crystal display or other flat panel display substrate having coated thereon a polymer, photoresist or resist relief image of the invention.

The invention also includes novel methods for synthesis of monomers and polymers of the invention. More specifically, methods are provided for synthesis of a norbornene monomer substituted with a photoacid-labile group, including a tertiary alicyclic ester, without isolation of any intermediates in a multiple-step synthesis.

More particularly, such monomer syntheses include e.g. reactions of, without isolation of intermediates (one-pot synthesis):

1) addition/reduction reaction of an alicyclic ketone, typically with an alkylating reagent such as a $C_{1-8}$ alkylating reagent such as Grignard reagent, particularly an alkyl-Grignard reagent such as $C_{1-8}$Mghalide, typically $C_{1-8}$MgBr or $C_{1-8}$MgCl;

2) reaction of the resulting endocyclic alcohol with a reactive α, β-unsaturated compound, e.g. an acryloyl or methacryloyl halide, particularly acryloyl chloride or methacryloyl chloride;

3) Diels-Alder reaction of the product of step 2), preferably with cyclopentadiene, to provide a norbornene compound substituted with a photoacid-labile tertiary alicyclic ester, including compounds of Formulae I or II above. Step 1) is not necessary if an alicyclic alcohol is employed as a starting reagent. acting photoresist, exposed portions are rendered more soluble in a developer solution while areas not exposed remain comparatively less developer soluble.

In general, photoresist compositions comprise at least a resin binder component and a photoactive agent. Photoresist compositions are described in Deforest, *Photoresist Materials and Processes,* McGraw Hill Book Company, New York, ch. 2, 1975 and by Moreau, *Semiconductor Lithography, Principles, Practices and Materials,* Plenum Press, New York, ch. 2 and 4, both incorporated herein by reference for their teaching of photoresist compositions and methods of making and using the same.

More recently, chemically-amplified-type resists have been increasingly employed, particularly for formation of sub-micron images and other high performance applications. Such photoresists may be negative-acting or positive-acting and generally include many crosslinking events (in the case of a negative-acting resist) or deprotection reactions (in the case of a positive-acting resist) per unit of photogenerated acid. In the case of positive chemically-amplified resists, certain cationic photoinitiators have been used to induce cleavage of certain "blocking" groups pendant from a photoresist binder, or cleavage of certain groups that comprise a photoresist binder backbone. See, for example, U.S. Pat. Nos. 5,075,199; 4,968,581; 4,883,740; 4,810,613; and 4,491,628, and Canadian Patent Application 2,001,384. Upon cleavage of the blocking group through exposure of a coating layer of such a resist, a polar functional group is formed, e.g., carboxyl or imide, which results in different solubility characteristics in exposed and unexposed areas of the resist coating layer. See also R. D. Allen et al., *Proceedings of SPIE,* 2724:334–343 (1996); and P. Trefonas et al. *Proceedings of the 11$^{th}$ International Conference on Photopolymers (Soc. Of Plastics Engineers),* pp 44–58 (Oct. 6, 1997).

While currently available photoresists are suitable for many applications, current resists also can exhibit significant shortcomings, particularly in high performance Other aspects of the invention are disclosed infra.

DETAILED DESCRIPTION OF THE INVENTION

References herein to a "tertiary alicyclic ester group" or other similar term indicate that a tertiary alicyclic ring carbon is covalently linked to the ester oxygen, i.e. —C(=O)O—TR where T is a tertiary ring carbon of alicyclic group R. In at least many cases, preferably a tertiary ring carbon of the alicyclic moiety will be covalently linked to the ester oxygen, such as exemplified by the above depicted preferred alicyclic moieties. However, the tertiary carbon linked to the ester oxygen also can be exocyclic to the alicyclic ring, typically where the alicyclic ring is one of the substituents of the exocyclic tertiary carbon. Typically, the tertiary carbon linked to the ester oxygen will be substituted by the alicyclic ring itself, and/or one, two or three alkyl groups having 1 to about 12 carbons, more typically 1 to about 8 carbon, even more typically 1, 2, 3, or 4 carbons. The alicyclic ring also preferably does not contain any aromatic substitution.

As stated above, polymers of the invention comprise one or more repeat units of a polymerized norbornene carboxylate esterified with photo acid-labile tertiary alicyclic group. Preferred polymers of the invention comprise one or more polymerized repeat units of compounds of Formula I and/or II as those formulae are defined above.

As discussed, various moieties, including moieties of compounds of Formulae I and/or II may be optionally substituted. A "substituted" substituent may be substituted at one or more available positions, typically 1, 2, or 3 positions by one or more suitable groups such as e.g. halogen (particularly F, Cl or Br); $C_{1-8}$ alkyl; $C_{1-8}$ alkoxy; $C_{2-8}$ alkenyl; $C_{2-8}$ alkynyl; hydroxyl; alkanoyl such as a $C_{1-6}$ alkanoyl e.g. acyl and the like; etc Polymers of the invention can be prepared by a variety of methods. One suitable method is free radical polymerization, e.g., by reaction of selected monomers to provide the various units as discussed above in the presence of a radical initiator under an inert atmosphere (e.g., $N_2$ or argon) and at elevated temperatures such as about 70° C. or greater, although reaction temperatures may vary depending on the reactivity of the particular reagents employed and the boiling point of the reaction solvent (if a solvent is employed). Suitable reaction solvents include e.g. tetrahydrofuran, ethyl lactate and the like. Suitable reaction temperatures for any particular system can be readily determined empirically by those skilled in the art based on the present disclosure. A variety of free radical initiators may be employed. For example, azo compounds may be employed such as azobis-2,4-dimethylpentanenitrile. Peroxides, peresters, peracids and persulfates also could be employed. See the examples which follow for exemplary reagents and conditions for synthesis of polymers of the invention.

Preferably a polymer of the invention will have a weight average molecular weight ($M_w$) of 1,000 to about 100,000, more preferably about 2,000 to about 30,000, still more preferably from about 2,000 to 15,000 or 20,000, with a molecular weight distribution ($M_w$,$M_n$) of about 3 or less, more preferably a molecular weight distribution of about 2 or less. Molecular weights (either $M_w$, or $M_n$) of the polymers of the invention are suitably determined by gel permeation chromatography.

Polymers of the invention also may contain aromatic units, such as polymerized vinylphenol, styrene units and the like. Such aromatic units are particularly suitable for polymers used in photoresists imaged at 248 nm. However, as discussed above, for even shorter wavelength imaging, such as 193 nm, preferably a polymer is substantially, essentially or completely free of aromatic units.

Polymers of the invention used in photoresist formulations should contain a sufficient amount of photogenerated acid labile ester groups to enable formation of resist relief images as desired. For instance, suitable amount of such acid labile ester groups will be at least 1 mole percent of total units of the polymer, more preferably about 2 to 50 mole percent, still more typically about 3 to 30 or 40 mole percent of total polymer units. See the examples which follow for exemplary preferred polymers.

As discussed above, synthetic methods are provided to produce norbornene compounds that contain a photoacid-labile moiety, including photoacid-labile tertiary alicyclic esters. Preferred synthetic methods of the invention are exemplified by the following Scheme:

SCHEME

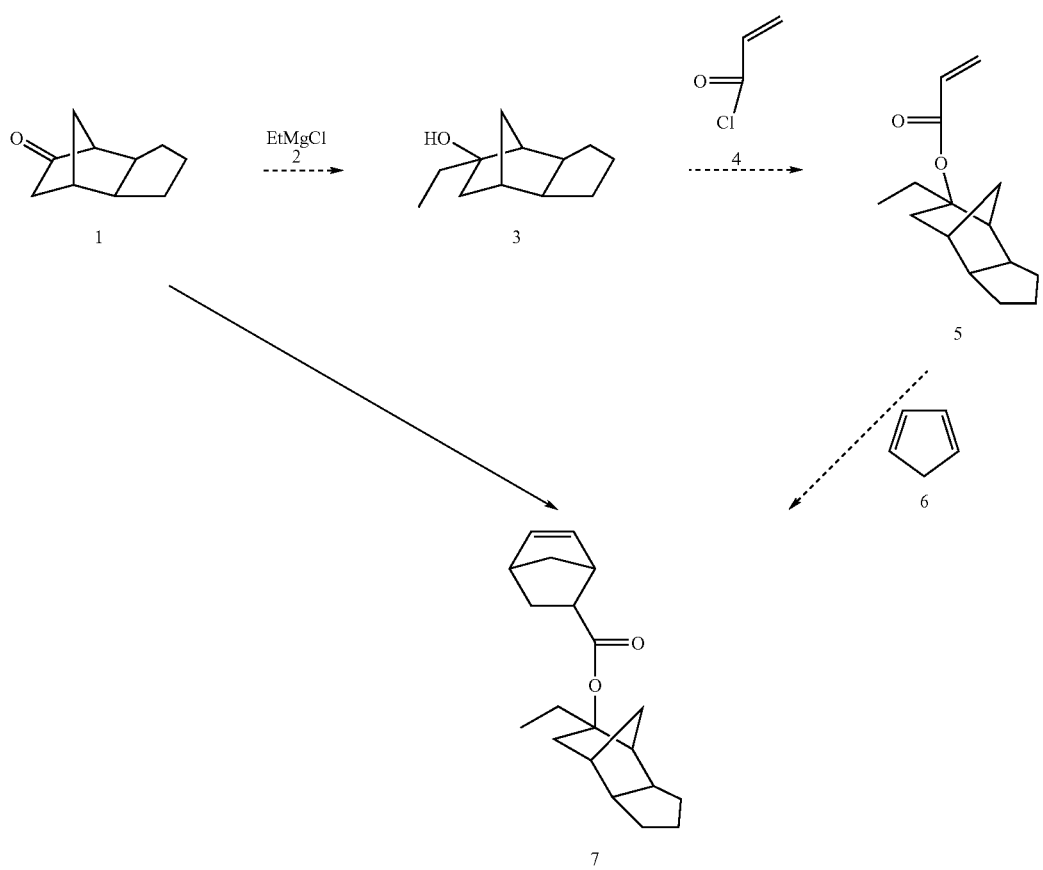

Other examples:

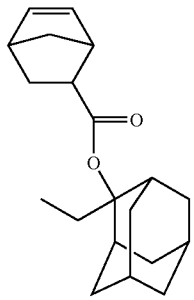

8

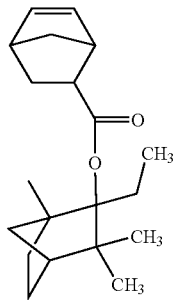

9

As shown in the above Scheme, alicyclic ketone 1 (carbonyl being a ring member; tricyclodecan-8-one depicted in the Scheme) is reduced to the related alcohol, preferably by in an addition reaction, particularly by reaction with an alkylating reagent, preferably a Grignard reagent 2 to provide the tertiary alicyclic alcohol 3 (alcohol being a ring member). Such a Grignard reaction is preferably conducted under reduced temperatures, particularly less than about 0° C., such as about −25° C. Preferably the alicyclic ketone is added over time (e.g. over 0.5, 1, 2, 3 or 4 or more hours) to a solution of the Grignard reagent maintained at reduced temperatures. The reaction is preferably conducted in a suitable solvent, such as an aprotic solvent, e.g. THF. Both the Grignard reagent and the alicyclic ketone can be admixed in such solvent. After the addition of the alicyclic is complete, the reaction can be stirred, preferably at somewhat elevated temperatures.

Thereafter, without isolation or other work-up of the addition reaction product 3, reactive α,β-unsaturated compound 4 is added directly to the reaction mixture that contains tertiary alcohol 3. Preferably, the α,β-unsaturated compound 4 is added over time (e.g. over 0.5, 1, 2, 3 or 4 or more hours) to a solution of the reaction mixture that contains 3 that is at a reduced temperature, e.g. less than about 0° C., such as about −25° C. Preferably, the reaction mixture is allowed to stir for an extended period (e.g. 2, 4, 6, 8, 10, 12, 14 or 16 hours or more) after the addition the α,β-unsaturated compound 4 is complete, and the reagents 3 and 4 can be allowed to warm from reduced temperature, e.g. to room temperature, to provide the tertiary ester 5.

Thereafter, the reaction mixture that contains ester 5 can be directly (without isolation or other work-up of the addition reaction product 5), reacted (Diels-Alder) reaction with a diene, particularly cyclopentadiene, which preferably is freshly cracked. After the diene addition is complete, preferably the reaction mixture is stirred for an extended period, e.g. 10, 20, 30, 40, 50, 60, 70, 80 hours or more, and at an elevated temperature, e.g. at least about 40° C., 50° C., or 60° C. to provide the norbornene with tertiary alicyclic ester 7. The Scheme also shows other illustrative compounds 8 and 9 that can be prepared by similar route starting with adamantyl ketone and ethyl fenchol respectively (synthesis starting with ethyl fenchol would omit alkylating reaction with Grignard reagent). See the examples which follow for exemplary preferred reaction conditions.

In the one-pot synthesis of the invention, preferably the reaction is conducted under anhydrous conditions. Thus, for example, the reactions preferably proceed under an inert atmosphere ($N_2$ or argon) and dry solvents are employed. As discussed above, the several reactions of the one-pot synthesis proceed without any isolation or other work-up of reaction products of any single stage of the synthesis.

Moreover, it has been found that this one-pot synthesis proceeds to provide a norbornene monomer with photoacid-labile tertiary alicyclic ester (compound 7, 8 or 9 above) in high yields from a starting material of alicyclic ketone (compound 1 above). For instance, norbornene monomer with photoacid-labile tertiary alicyclic ester (compound 7, 8 or 9 above) can be obtained in at least 30 or 40 percent yields from a starting material of an alicyclic ketone (e.g. compound 1 above), or even higher yields such as at least 50, 60, 70, 75 or 80 percent yields from a starting material of an alicyclic ketone (e.g. compound 1 above).

As discussed above, the polymers of the invention are highly useful as a resin binder component in photoresist compositions, particularly chemically-amplified positive resists. Photoresists of the invention in general comprise a photoactive component and a resin binder component that comprises a polymer as described above.

The resin binder component should be used in an amount sufficient to render a coating layer of the resist developable with an aqueous alkaline developer.

The resist compositions of the invention also comprise a photoacid generator (i.e. "PAG") that is suitably employed in an amount sufficient to generate a latent image in a coating layer of the resist upon exposure to activating radiation. Preferred PAGs for imaging at 193 nm and 248 nm imaging include imidosulfonates such as compounds of the following formula:

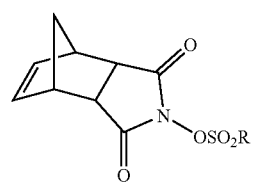

wherein R is camphor, adamantane, alkyl (e.g. $C_{1-12}$ alkyl) and perfluoroalkyl such as perfluoro($C_{1-12}$alkyl), particularly perfluorooctanesulfonate, perfluorononanesulfonate and the like. A specifically preferred PAG is N-[(perfluorooctanesulfonyl)oxy]-5-norbornene-2,3-dicarboximide.

Sulfonate compounds are also suitable PAGs, particularly sulfonate salts. Two suitable agents for 193 nm and 248 nm imaging are the following PAGS 1 and 2:

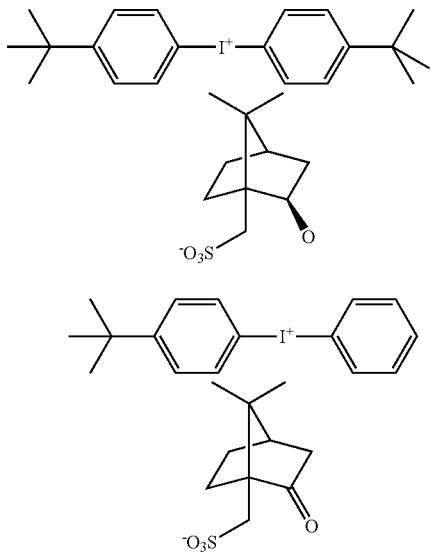

Such sulfonate compounds can be prepared as disclosed in European Patent Application 96118111.2 (publication number 0783136), which details the synthesis of above PAG 1.

Also suitable are the above two iodonium compounds complexed with anions other than the above-depicted camphorsulfonate groups. In particular, preferred anions include those of the formula $RSO_3^-$ where R is adamantane, alkyl (e.g. $C_{1-12}$ alkyl) and perfluoroalkyl such as perfluoro ($C_{1-12}$ alkyl), particularly perfluorooctanesulfonate, perfluorobutanesulfonate and the like.

Other known PAGS also may be employed in the resists of the invention. Particularly for 193 nm imaging, generally preferred are PAGS that do not contain aromatic groups, such as the above-mentioned imidosulfonates, in order to provide enhanced transparency.

A preferred optional additive of resists of the invention is an added base, particularly tetrabutylammonium hydroxide (TBAH), or tetrabutylammonium lactate, which can enhance resolution of a developed resist relief image. For resists imaged at 193 nm, a preferred added base is a hindered amine such as diazabicyclo undecene or diazabicyclononene. The added base is suitably used in relatively small amounts, e.g. about 0.03 to 5 percent by weight relative to the total solids.

Photoresists of the invention also may contain other optional materials. For example, other optional additives include anti-striation agents, plasticizers, speed enhancers, etc. Such optional additives typically will be present in minor concentrations in a photoresist composition except for fillers and dyes which may be present in relatively large concentrations, e.g., in amounts of from about 5 to 30 percent by weight of the total weight of a resist's dry components.

The compositions of the invention can be readily prepared by those skilled in the art. For example, a photoresist composition of the invention can be prepared by dissolving the components of the photoresist in a suitable solvent such as, for example, ethyl lactate, ethylene glycol monomethyl ether, ethylene glycol monomethyl ether acetate, propylene glycol monomethyl ether; propylene glycol monomethyl ether acetate and 3-ethoxyethyl propionate. Typically, the solids content of the composition varies between about 5 and 35 percent by weight of the total weight of the photoresist composition. The resin binder and photoactive components should be present in amounts sufficient to provide a film coating layer and formation of good quality latent and relief images. See the examples which follow for exemplary preferred amounts of resist components.

The compositions of the invention are used in accordance with generally known procedures. The liquid coating compositions of the invention are applied to a substrate such as by spinning, dipping, roller coating or other conventional coating technique. When spin coating, the solids content of the coating solution can be adjusted to provide a desired film thickness based upon the specific spinning equipment utilized, the viscosity of the solution, the speed of the spinner and the amount of time allowed for spinning.

The resist compositions of the invention are suitably applied to substrates conventionally used in processes involving coating with photoresists. For example, the composition may be applied over silicon wafers or silicon wafers coated with silicon dioxide for the production of microprocessors and other integrated circuit components. Aluminum-aluminum oxide, gallium arsenide, ceramic, quartz, copper, glass substrates and the like are also suitably employed.

Following coating of the photoresist onto a surface, it is dried by heating to remove the solvent until preferably the photoresist coating is tack free. Thereafter, it is imaged through a mask in conventional manner. The exposure is sufficient to effectively activate the photoactive component of the photoresist system to produce a patterned image in the resist coating layer and, more specifically, the exposure energy typically ranges from about 1 to 100 mJ/cm$^2$, dependent upon the exposure tool and the components of the photoresist composition.

As discussed above, coating layers of the resist compositions of the invention are preferably photoactivated by a short exposure wavelength, particularly a sub-300 and sub-200 nm exposure wavelength. Particularly preferred exposure wavelengths include 193 nm and 248 nm. However, the resist compositions of the invention also may be suitably imaged at higher wavelengths. For example, a resin of the invention can be formulated with an appropriate PAG and used as a chemically-amplified positive I-line resist, i.e. a resist imaged at about 365 nm.

Following exposure, the film layer of the composition is preferably baked at temperatures ranging from about 70° C. to about 160° C. Thereafter, the film is developed. The exposed resist film is rendered positive working by employing a polar developer, preferably an aqueous based developer such as quaternary ammonium hydroxide solutions such as a tetra-alkyl ammonium hydroxide solution; various amine solutions preferably a 0.26 N tetramethylammonium hydroxide, such as ethyl amine, n-propyl amine, diethyl amine, di-n-propyl amine, triethyl amine, or methyldiethyl amine; alcohol amines such as diethanol amine or triethanol amine; cyclic amines such as pyrrole, pyridine, etc. In general, development is in accordance with procedures recognized in the art.

Following development of the photoresist coating over the substrate, the developed substrate may be selectively processed on those areas bared of resist, for example by chemically etching or plating substrate areas bared of resist in accordance with procedures known in the art. For the manufacture of microelectronic substrates, e.g., the manufacture of silicon dioxide wafers, suitable etchants include a gas etchant, e.g. a chlorine or fluorine-based etchant such a $Cl_2$ or $CF_4/CHF_3$ etchant applied as a plasma stream. After such processing, resist may be removed from the processed substrate using known stripping procedures.

All documents mentioned herein are incorporated herein by reference. The following non-limiting examples are illustrative of the invention.

EXAMPLES 1–3

Syntheses of Monomers

EXAMPLE 1

Norbornene ethyl tricyclodecane carboxylate monomer synthesis

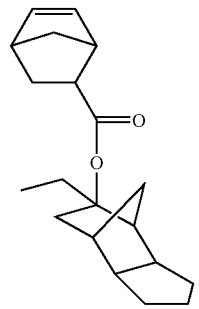

| Material | Amt (g) | Amt (ml) | Moles | Source |
|---|---|---|---|---|
| Tricyclodecan-8-one | 153.6 | | ~1.02 | TCI |
| Ethylmagnesiumchloride (25%) | 400 | ~388 | ~1.12 | ACROS |
| Acryloyl chloride | 108 | ~96.9 | ~1.19 | Aldrich |
| Tetrahydrofuran | 480 | 540 | | Aldrich |
| Cyclopentadiene | 75 | | ~1.12 | ACROS |

All reaction glassware was dried in the oven overnight at 100° C. The glassware was set up and cooled under a stream of nitrogen. The reaction was carried out under a blanket of nitrogen.

To a 2 L flask fitted with a gas inlet, thermometer, overhead stirrer and a rubber septum was added 400 g of ethylmagnesium chloride, 25 wt % solution in tetrahydrofuran (THF) via a double tipped needle using nitrogen pressure. The mixture was cooled to −25 to −30° C. using a dry ice/isopropanol bath. While the ethylmagnesium chloride solution was cooling the 153.6 g of tricyclodecan-8-one was dissolved in 480 g of tetrahydrofuran. To a 1L flask equipped with a gas inlet, glass stopper and a rubber septum was added the 153.6 g of tricyclodecan-8-one. The anhydrous, inhibitor free tetrahydrofuran was transferred to the 1L flask via a double tipped needle using nitrogen pressure. When the ethylmagnesium chloride was at −25 to −30° C., the tricyclodecan-8-one/THF solution was transferred over a 2 hr period to the 2L flask containing the ethylmagnesium chloride via a double tipped needle using nitrogen pressure. The cooling bath was removed and the reaction mixture was stirred for 2 hr. After stirring for 2 hr the mixture was again cooled to −25 to −30° C. using a dry ice/isopropanol bath. The acryloyl chloride (108 g) was then added dropwise over a 1.25–1.5 hour period using a 125 ml pressure equalizing dropping funnel. The reaction was allowed to come to room temperature with overnight stirring. A white precipitate developed from the clear amber colored reaction solution. After stirring overnight, freshly cracked cyclopentadiene (75 g) was added dropwise at room temperature over 30 minutes using a 125 ml pressure equalizing dropping funnel. The mixture was then heated for 68 hr at 50° C. The reaction mixture was now orange in color with a white precipitate present. The reaction was cooled to room temperature. Water (DI) was added until all of the salts had dissolved (~400 ml) and two distinct layer were seen. The layers were separated and the organic (upper) layer was dried over magnesium sulfate. The THF was removed leaving 310 g of an orange oil. The orange oil was dissolved in 1.5 L of hexane then washed with 1×500 ml saturated aqueous sodium bicarbonate solution and 2×500 ml DI water. The layers were separated and the organic layer dried over magnesium sulfate. The hexane was removed leaving ~300 g of an orange oil. The oil was distilled under reduced pressure (158° C./5 mm) leaving 189 g of pure norbornene ethyl tricyclodecane carboxylate.

EXAMPLE 2

Synthesis of norbornene methyl tricyclodecane carboxylate

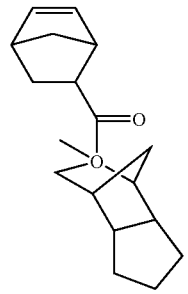

A solution of 125 ml of 1.4 M methyl lithium (in ethyl ether) in 100 ml of hexane was decanted into a three neck round-bottom flask at an ice-water bath. To it, a solution of 24.00 g of tricyclo[5.2.1.0]decan-8-one in hexane was added dropwise. After addition, the reaction mixture was stirred for 4 hours at 0° C. Then, a solution of 13 ml of acroyl chloride in 50 ml of hexane was added dropwise at 0° C. After addition, the reaction mixture was stirred at the same bath for overnight (16 hours). Next, 11 g of cyclopentadiene in 50 mL of hexane was dropwise to the reaction mixture at ice/water bath. After the addition, the ice/water bath was removed and the reaction mixture was heated to 50° C. for 48 hrs. During the periods, lots of white precipitation were found. After filtering the white salts, the organic layer was washed with $NaHCO_3$ (sat aq) and water three times (3×300 ml). Then, the washed organic layer was dried over anhydrous $MgSO_4$. The organic solvent was removed by a rotary pump to give the crude title monomer. The monomer was purified by a reduced pressure (5 mmHg/154–158° C.) to give the norbornene methyltricyclodecane carboxylate (yields: 72%).

EXAMPLE 3

Synthesis of Norbornene ethyl fenchol carboxylate

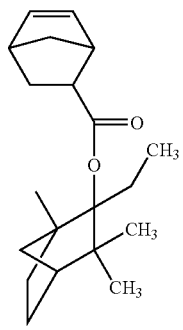

A solution of 230 ml of 2.5 M n-butyl lithium in 50 ml of THF was decanted into a three neck round-bottom flask at an ice-water bath. To it, a solution of 100 g of ethyl fenchol in 50 ml THF was added dropwise. After addition, the reaction mixture was stirred for 24 hours at 0° C. Then, a solution of 59.88 g of acroyl chloride in 150 ml of THF was added dropwise at 0° C. After addition, the reaction mixture was stirred at the same bath for overnight (16 hours). Next, 40 g of cyclopentadiene in 50 mL of hexane was dropwise to the reaction mixture at ice/water bath. After the addition, the ice/water bath was removed and the reaction mixture was heated to 50° C. for 48 hrs. During the periods, lots of white precipitation were found. After filtering the white salts, the organic layer was washed with $NaHCO_3$ (sat aq) and water three times (3×300 ml). Then, the washed organic layer was dried over anhydrous $MgSO_4$. The organic solvent was removed by a rotary pump to give the crude title monomer. The monomer was purified by a reduced pressure (5 mmHg/ 145–148° C.) to give the norbornene ethylfenchol carboxylate (yields: 64%).

EXAMPLES 4–5

Polymer syntheses

EXAMPLE 4

COMA terpolymer (molar ratio of norbomenelactone:norborneester:maleic anhydride=12.5/37.5/50)

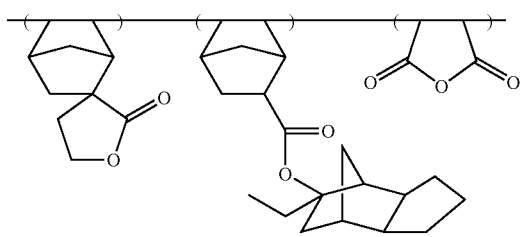

A mixture of Norbornene ethyltricyclodecane carboxylate (15.16 g), maleic anhydride (6.60 g), norbornene-spiro-butylactone (2.80 g), and V601 (0.31 g, 1% mole of total monomers) in 12.28 g ethylacetate was placed in a round-bottomed flask. After stirred for 5 minutes (until all solid were dissolved in the solvent), the flask was put into a pre-heat 70° C. oil bath. The reaction mixture was stirred at this temperature for 24 hours. After cooling, to this flask, 25.0 g of THF was added. The polymer was isolated by precipitation into 1.5 L of hexane/IPA (1/1, % wt.). The suspension mixture was stirred for 120 minutes. Then, the polymer was filtered off and washed the polymer by additional 200 mL of hexane. The polymer was dried in a vacuum oven at 40 ° C. for overnight (about 16 hours). Yield=25%.

EXAMPLE 5

Tetrapolymer: norborene/(spiro-2-2-α-butyrolactone)-5-norborene/norbornene ethyl tricyclodecane carboxylate /maleic anhydride (molar ratio of respective units: 7.5:7.5:35:50).

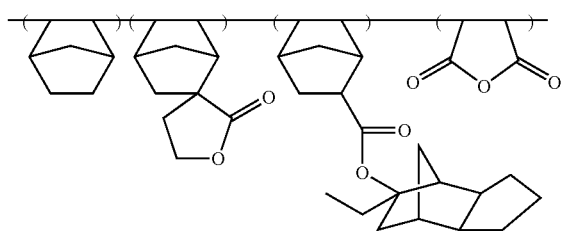

Into a 100 ml Round bottom flask the following was weighted out:

| | |
|---|---|
| Norbornene | 1.22 grams (0.013 moles) |
| (spiro-2-2-α-butyrolactone)-5-Norbornene | 2.13 grams (0.013 moles) |
| Maleic Anhydride | 8.86 grams (0.086 moles) |
| Norbornene ethyl tricyclodecane carboxylate | 18.18 grams (0.060 moles) |
| V601 | 0.4 grams (0.0017 moles) |
| 15 grams Ethyl acetate | |

A magnetic stir bar was added to the flask and the solution was stirred for ~15 minutes to dissolve the contents of the flask. Once in solution the flask was placed in a hot oil bath that was preheated to 80° C. A condenser and $N_2$ line was attached on top and the reaction was allowed to stir for 24 hours. After 24 hours the heat was removed and the flask was allowed to cool to room temperature. After cooling to room temperature the contents of the flask was precipitated into 1.5 L (of 50/50 hexanes/IPA w/w). The precipitated solution was stirred for 1.5 hours and then the polymer was isolated, via a glass fretted funnel. The polymer was then dried for 4 hours in the hood and then overnight in a vacuum oven, at room temperature. This reaction yielded 15 grams/30 grams of polymer, giving a 50% yield. This reaction was later repeated at a 20 gram scale and the oil bath heated to 90° C. This gave 11.21 grams/20 grams (56% yield).

EXAMPLE 6

Photoresist preparation and lithographic processing

A photoresist of the invention is prepared by mixing the following components with amounts expressed as weight percent based on total weight of the resist compositions:

| Resist components | Amount (wt. %) |
| --- | --- |
| Resin binder | 15 |
| Photoacid generator | 4 |
| Ethyl lactate | 81 |

The resin binder is the polymer of Example 4 above. The photoacid generator is di-(4-t-butyl)iodonium(+/−)-10-camphor sulfonate (PAG 1 above). Those resin and PAG components are admixed in the ethyl lactate solvent.

The formulated resist composition is spin coated onto HMDS vapor primed 4 inch silicon wafers and softbaked via a vacuum hotplate at 90° C. for 60 seconds. The resist coating layer is exposed through a photomask at 193 nm, and then the exposed coating layers are post-exposure baked at 110° C. The coated wafers are then treated with 0.26 N aqueous tetramethylammonium hydroxide solution to develop the imaged resist layer and provide a relief image.

The foregoing description of the invention is merely illustrative thereof, and it is understood that variations and modification can be made without departing from the spirit or scope of the invention as set forth in the following claims.

What is claimed is:

1. A method for forming a photoresist relief image, comprising:
   (A) providing a monomer of the following Formula I:

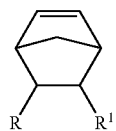

wherein R and R¹ are independently hydrogen, an ester moiety with a tertiary alicyclic group, optionally substituted alkyl, optionally substituted alkoxy, with at least one of R and R¹ being an ester moiety with a tertiary polycyclic alicyclic group,
   by steps comprising:
   (i) reacting an alicyclic alcohol with an α,β-unsaturated compound to provide an α,β-unsaturated ester;
   (ii) reacting the α,β-unsaturated ester with a diene to provide a norbornene compound,
      steps i) and ii) being conducted without isolation of the α,β-unsaturated ester prior to reaction with the diene;
   (B) providing a positive-acting photoresist composition by steps comprising:
   (a) providing an admixture of a photoactive component and polymer that comprises phenyl groups and repeat units of a polymerized monomer of Formula I and produced in step (A);
   (C) applying a coating layer of the photoresist composition on a substrate; and
   (D) exposing the photoresist composition coating layer to activating radiation and developing the exposed photoresist composition layer to yield a relief image.

2. The method of claim 1 wherein the polymer comprises further comprises acrylate groups that comprise photoacid-labile moieties.

3. The method of claim 1 wherein the monomer corresponds to the following formula:

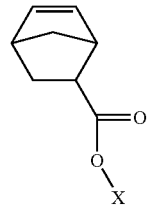

wherein X is a tertiary alicyclic group.

4. The method of claim 1 wherein the photoresist composition layer is exposed with radiation having a wavelength of about 193 nm.

5. The method of claim 1 wherein the photoresist composition layer is exposed with radiation having a wavelength of about 248 nm.

6. The method of claim 1 wherein steps (i) and (ii) are conducted in the same reaction vessel.

7. The method of claim 1 further comprising a step ai) of reacting an alicyclic ketone with an alkylating agent to provide the alicyclic alcohol.

8. The method of claim 7 wherein steps ai), i) and ii) are conducted without isolation of intermediate compounds.

9. The method of claim 8 wherein steps ai), i) and ii) are conducted in the same reaction vessel.

10. The method of claim 1 wherein the α,β-unsaturated compound is an acryloyol halide or methacryol halide.

11. The method of claim 1 wherein the diene is cyclopentadiene.

12. A positive-acting photoresist composition comprising a photoactive component and a polymer comprising i) phenyl groups and ii) repeat units that comprise a polymerized monomer of the following Formula I:

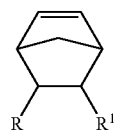

wherein R and R¹ are independently hydrogen, an ester moiety with a tertiary alicyclic group, an optionally substituted alkyl, optionally substituted alkoxy, with at least one of R and R¹ being an ester moiety with a tertiary alicyclic group,
   and wherein the monomer of Formula I is obtainable by steps comprising:
   a) reacting an alicyclic alcohol with an α,β-unsaturated compound to provide an α,β-unsaturated ester;
   b) reacting the α,β-unsaturated ester with a diene to provide a norbornene compound, and the α,β-unsaturated ester is not isolated prior to reaction with the diene.

13. The photoresist composition of claim 12 wherein the polymer comprises further comprises acrylate groups that comprise photoacid-labile moieties.

14. A positive-acting photoresist composition comprising a photoactive component and a polymer comprising i) phenyl groups and ii) repeat units that comprise a polymerized monomer of the following Formula I:

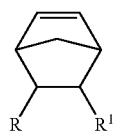

I wherein R and R¹ are independently hydrogen, an ester moiety with a tertiary alicyclic group, an optionally substituted alkyl, optionally substituted alkoxy, with at least one of R and R¹ being an ester moiety with a tertiary alicyclic group.

15. The photoresist composition of claim 14 wherein the polymer comprises further comprises acrylate groups that comprise photoacid-labile moieties.

* * * * *